United States Patent
Morrison, III et al.

(10) Patent No.: US 9,114,021 B2
(45) Date of Patent: Aug. 25, 2015

(54) METHOD FOR PROVIDING DISC NUCLEUS REPLACEMENT IN A SPINE

(71) Applicant: MEDGEM, LLC, Atlanta, GA (US)

(72) Inventors: Thomas J. Morrison, III, Atlanta, GA (US); Mara Morrison, Atlanta, GA (US); Joseph William Pruitt, Athens, GA (US); Thomas Richard Ellis, Lawrenceville, GA (US); George Samuel Brockway, II, Lawrenceville, GA (US)

(73) Assignee: Medgem, LLC, Atlanta, GA (US)

( * ) Notice: Subject to any disclaimer, the term of this patent is extended or adjusted under 35 U.S.C. 154(b) by 373 days.

(21) Appl. No.: 13/653,004

(22) Filed: Oct. 16, 2012

(65) Prior Publication Data

US 2013/0041470 A1   Feb. 14, 2013

Related U.S. Application Data

(60) Division of application No. 12/726,112, filed on Mar. 17, 2010, now abandoned, which is a continuation-in-part of application No. 12/134,946, filed on Jun. 6, 2008, now Pat. No. 9,005,290.

(60) Provisional application No. 60/942,802, filed on Jun. 8, 2007.

(51) Int. Cl.
*A61F 2/44* (2006.01)
*A61F 2/30* (2006.01)

(52) U.S. Cl.
CPC .............. *A61F 2/442* (2013.01); *A61F 2/4455* (2013.01); *A61F 2/30965* (2013.01); *A61F 2002/30014* (2013.01); *A61F 2002/3025* (2013.01); *A61F 2002/30242* (2013.01); *A61F 2002/30245* (2013.01); *A61F 2002/30448* (2013.01); *A61F 2002/30563* (2013.01); *A61F 2002/30565* (2013.01); *A61F 2002/30616* (2013.01); *A61F 2002/444* (2013.01); *A61F 2220/005* (2013.01); *A61F 2230/0071* (2013.01); *A61F 2250/0018* (2013.01); *A61F 2310/00017* (2013.01);
(Continued)

(58) Field of Classification Search
USPC ........................................... 623/17.11, 17.16
See application file for complete search history.

(56) References Cited

U.S. PATENT DOCUMENTS

| | | | |
|---|---|---|---|
| 1,426,712 | A | 8/1922 | Chatfield |
| 5,531,614 | A | 7/1996 | Gallusser et al. |
| 5,534,028 | A | 7/1996 | Bao et al. |

(Continued)

FOREIGN PATENT DOCUMENTS

| | | |
|---|---|---|
| DE | 4423826 A1 | 1/1995 |
| WO | 02087480 A1 | 11/2002 |

(Continued)

OTHER PUBLICATIONS

"Medtronic Sofamor Danek 510(k): Satellite Spinal System," Aug. 2005, Department of Health & Human Services, Food and Drug Administration, Rockville, MD.

*Primary Examiner* — Christian Sevilla
(74) *Attorney, Agent, or Firm* — Hunton & Williams, LLP (57) ABSTRACT

A spinal interbody device includes a compliant inner dampener in combination with a rigid outer material of outer shells. An inner dampener includes a rim with pillars and heads coupled to a complimentary inner structure of the outer shells.

20 Claims, 5 Drawing Sheets

(52) U.S. Cl.
CPC ............... *A61F2310/00023* (2013.01); *A61F 2310/00029* (2013.01)

(56) References Cited

U.S. PATENT DOCUMENTS

| | | |
|---|---|---|
| 5,865,846 A | 2/1999 | Bryan et al. |
| 5,888,150 A | 3/1999 | Young |
| 6,348,071 B1 | 2/2002 | Steffee et al. |
| 6,419,704 B1 | 7/2002 | Ferree |
| 6,582,468 B1 | 6/2003 | Gauchet |
| 6,629,898 B2 | 10/2003 | Nardacci |
| 6,773,363 B2 | 8/2004 | Sullivan |
| 7,025,787 B2 | 4/2006 | Bryan et al. |
| 7,214,245 B1 | 5/2007 | Marcolongo et al. |
| 2002/0052461 A1 | 5/2002 | Forschner et al. |
| 2003/0220691 A1 | 11/2003 | Songer et al. |
| 2004/0010316 A1 | 1/2004 | William et al. |
| 2004/0030391 A1 | 2/2004 | Ferree |
| 2004/0054411 A1 | 3/2004 | Kelly et al. |
| 2004/0186576 A1 | 9/2004 | Biscup et al. |
| 2005/0085909 A1 | 4/2005 | Eisermann |
| 2006/0235528 A1 | 10/2006 | Buettner-Janz |
| 2007/0088441 A1 | 4/2007 | Duggal et al. |
| 2009/0088850 A1* | 4/2009 | Froehlich ............... 623/17.16 |

FOREIGN PATENT DOCUMENTS

| | | |
|---|---|---|
| WO | 03000952 A1 | 1/2003 |
| WO | 03094806 A1 | 11/2003 |
| WO | 2007084823 A2 | 7/2007 |

\* cited by examiner

Fig_11

METHOD FOR PROVIDING DISC NUCLEUS REPLACEMENT IN A SPINE

CROSS-REFERENCE TO RELATED APPLICATIONS

This application is divisional of U.S. patent application Ser. No. 12/726,112, filed Mar. 17, 2010, which is a continuation-in-part of U.S. patent application Ser. No. 12/134,946 filed Jun. 6, 2008, which claims priority to U.S. provisional patent application Ser. No. 60/942,802 filed Jun. 8, 2007, all of which are relied on and incorporated by reference.

BACKGROUND OF THE INVENTION

The present invention relates to fusion and non-fusion spinal interbody devices.

Spinal interbody devices such as the Fernstrom ball developed by Dr. Ulf Fernstrom, the Harmon Spinal Sphere of the Austenal Company (New York, N.Y.) and the more recent Satellite Spinal System of Medtronic Sofamar Danek (Memphis, Tenn.) have attempted stabilization in a disc interspace with an insertable solid sphere. Because of the rigidity and lack of compression of such solid spheres, undesirable subsidence of the device may result leading to possible nerve agitation and further corrective surgery.

Nucleus propulsus replacement has also been attempted with non-rigid hydrogels, such as disclosed in U.S. Pat. No. 7,214,245 to Marcolongo et al. Such hydrogels, however, are prone to migration and escape from the interbody space.

Accordingly, a need exists for a compressible spinal interbody device that avoids the problems of interbody devices that are either too rigid or too yielding.

SUMMARY OF THE INVENTION

In embodiments, the present invention answers this need by providing an interbody device with both rigid and compressible components for both supporting and absorbing axial loads while limiting subsidence and endplate erosion. The compressible components include material of greater compressibility than material of rigid components.

In one embodiment, rigid material may include, but is not limited to, biocompatible materials such as polyetheretherketone (PEEK), carbon fiber reinforced PEEK such as PEEK-Optima (Invibio, Inc., West Conshohocken, Pa.) and other biocompatible polymeric materials. In further embodiments, rigid material may include biocompatible metals, including without limitation titanium, stainless steel and cobalt chromium alone or in combination with other materials. In further embodiments, the compressible material may include, but not limited to, biocompatible materials such as elastomers, thermoplastic polyurethane elastomers such as Tecothane (Lubrizol Advanced Materials Inc., Wickliffe, Ohio), ultra high molecular weight polyethylene (UHMWPE), polycarbonate urethane (Sulene-PCU), polyethylene terephtalate (Sulene-PET), hydrogels (including with a polyethylene jacket), polyvinyl alcohol hydrogel (Aquarelle) and polycarbonate urethane elastomer (Newcleus) alone or in combination with other materials.

In embodiments of the invention, an interbody device includes top and bottom shells of a first material and an inner dampener of second dampening material. In one embodiment, top and bottom shells comprise a carbon fiber reinforced PEEK material and the inner dampener material of a thermoplastic polyurethane elastomer.

In some embodiments, a plurality of shell components may be coupled with an inner dampener material.

In alternative embodiments, an inner dampener may comprise a mechanical spring and like compressible components of various materials.

In one embodiment, an interbody device of the invention may be an ellipsoid, including but not limited to a sphere, oblate spheroid, prolate spheroid and scalene ellipsoids. In other embodiments of the invention an interbody device may compromise a partial ellipsoid, partial polyhedrons and other shapes configured to include top and bottom curved surface portions for contacting vertebral bodies.

In some embodiments, an interbody device includes an inner dampener having one or more ellipsoidal compressible core portions and a compressible equatorial planar surface portion extending outwardly from the core.

In some embodiments, a pillar support may extend outward from one or more ellipsoidal core portions of the inner dampener. In further embodiments one or more pillar supports may include a head with a larger diameter than a pillar, wherein the head couples within a complimentary receiving portion of an outer shell such that one or more heads secure the inner dampeners and its components, such as an equatorial planar surface portion, one or more compressible ellipsoidal core portions and one or more pillars, within the inner body device.

In embodiments of the invention, compressible and rigid materials may be combined through coupling means including, but not limited to, molding including overmolding and injection molding, press-fitting, adhesives, mechanical fastening and the like.

In embodiments of the invention, an interbody device of the present invention may be adapted for interbody fusion procedures to provide improved stabilization, stress-shielding and maintenance of placement in the interbody space. In other embodiments an interbody device of the present invention may be adapted for interbody non-fusion procedures to provide dynamic stabilization, stress-shielding, reduced movement, reduced likelihood of escape and reduced subsidence.

DESCRIPTION OF THE INVENTION

The present invention provides an apparatus for disc nucleus replacement to promote the support and absorption of axial loads while limiting subsidence and endplate erosion in both vertebral fusion and non-fusion spinal treatments. In non-fusion embodiments, the combination of rigid and compressible components with curved surface portions, including a smooth outer surface in embodiments, is adapted for placement and contacting the vertebral bodies to promote motion preservation and dynamic stabilization.

Although the invention is described in spherical embodiments, it will be appreciated that other ellipsoid shapes (including other spheroids) and still further various shapes that include curved surface portions configured to contact a vertebrae may be provided in other embodiments. The shaping, internal geometry and materials of an interbody device 10 of the invention in various embodiments supports spinal loads of preferably over 700 pounds and up to 1000 pounds without damage or disadvantageous alteration of the interbody device 10.

Referring to FIGS. 1-4 and 8, an interbody device 10 in one embodiment of the invention is a spherical shape. The device 10 includes a top outer shell 102, a bottom outer shell 104 and an inner dampener 200. The outer shells 102 and 104 may comprise sphere portions adapted to couple to inner dampener 200. In some embodiments the top outer shell 102 and bottom outer shell 104 may be identical in size and shape. In other embodiments the shells 102 and 104 may be differently sized or shaped. The outer shells may comprise relatively rigid biocompatible materials, including, but not limited to, PEEK or carbon fiber reinforced PEEK (such as PEEK-Optima), titanium, stainless steel, cobalt chromium and the like, either alone or in combination with these or other materials. In other embodiments the outer shells may include other rigid polymeric materials or other metal materials. In embodiments of the invention to promote dynamic stabilization and reduce friction, shells 102 and 104 include a smooth outer surface generally free of a frictional texture and protrusions.

Figure 8:
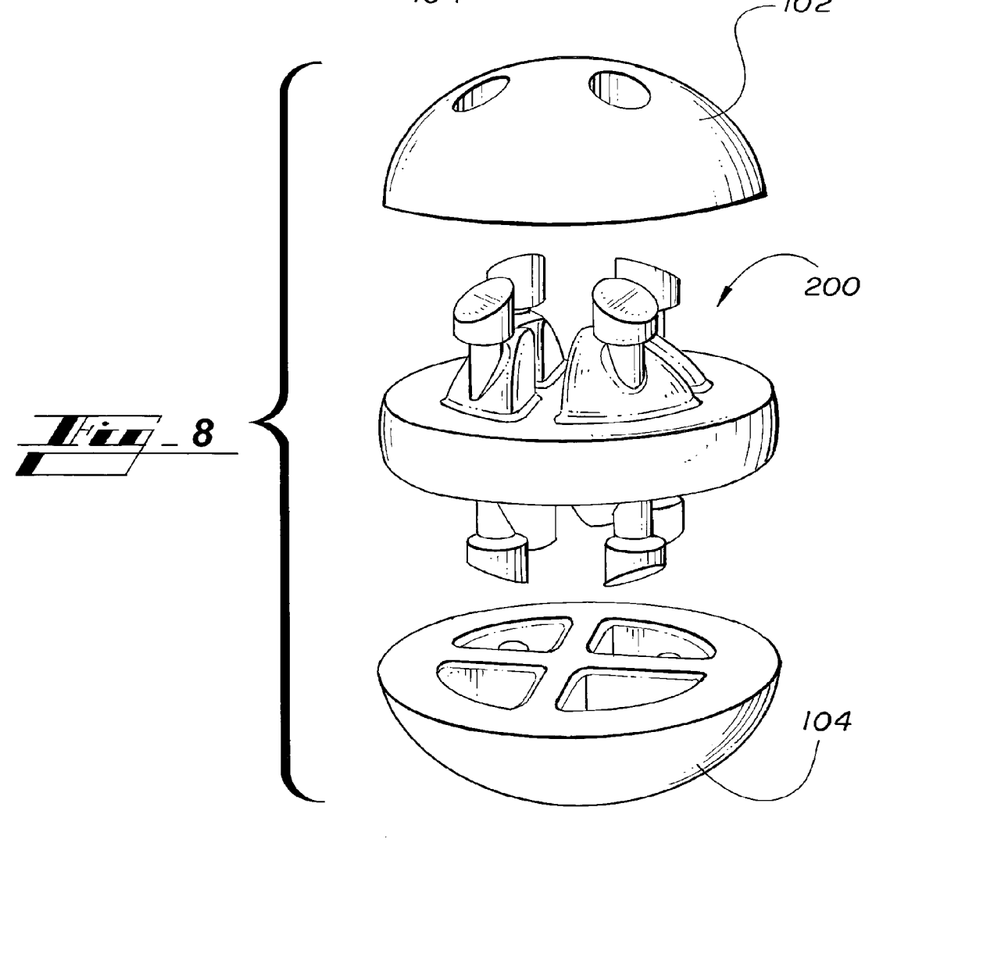
FIG. 8 is an exploded view of a spherical interbody device in one embodiment of the present invention.
Figure 10:
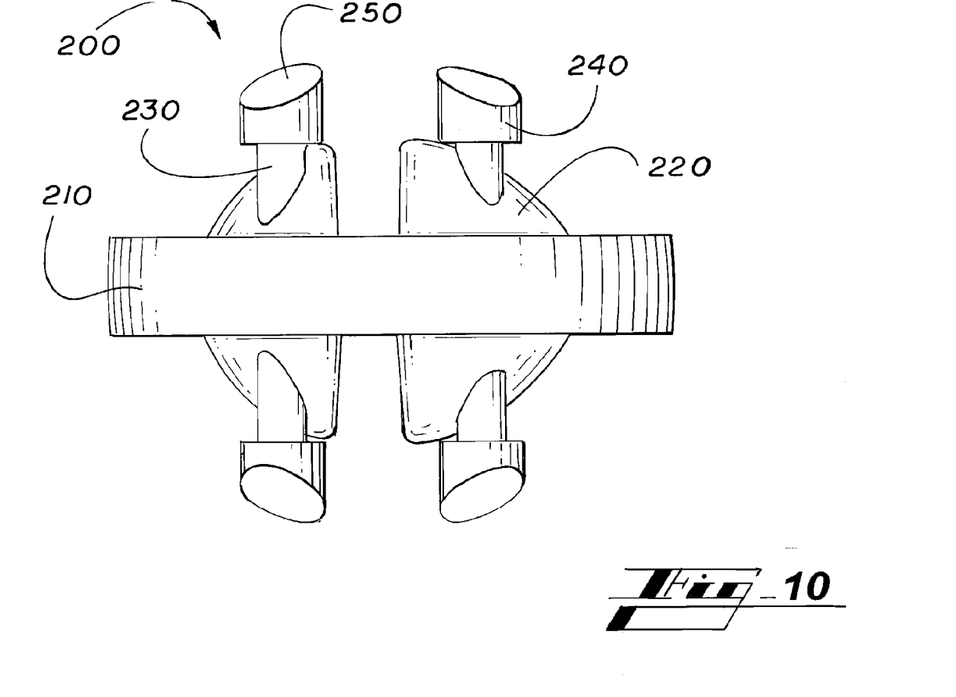
FIG. 10 is a front plan view of an inner dampener of a spherical interbody device in one embodiment of the present invention.
Figure 11:
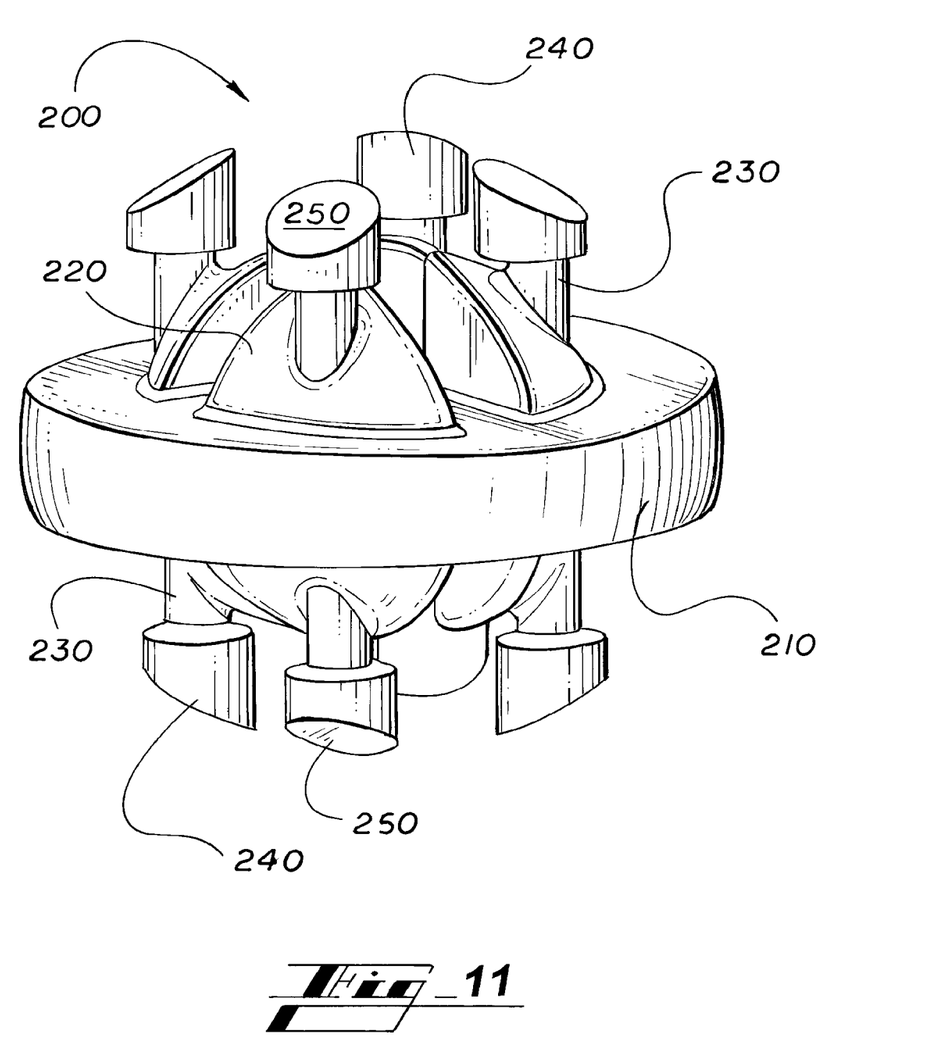
FIG. 11 is a perspective view of an inner dampener of a spherical interbody device in one embodiment of the present invention.

With continuing reference to FIG. 8 and further reference to FIGS. 10 and 11, in one embodiment of the invention inner dampener 200 is molded with a rim 210 as an equatorial planar surface portion coupled to convex ellipsoidal compressible core portions 220. From each convex core portion 220 a pillar 230 extends to a head 240. In one embodiment of the invention, each head 240 includes a slanted face 250 of a cylindrical segment of head 240. In one embodiment, the rim 210 has a diameter of about 11 mm and is about 2 mm thick. The pillar 230 has a diameter of about 1.27 mm and heads 240 have a diameter of about 1.88 mm. In embodiments the greater diameter of the heads 240 compared to the pillars 230 promotes securing the inner dampener 200 within outer shells 102 and 104. In embodiments, faces 250 also provide a continuous, smooth outer surface in combination with the outer shells.

The inner dampener 200 may comprise compressible material including, but not limited to, polyethylene, polycarbonate urethane (Sulene), polyethylene terephtalate (Sulene), HP-100 silicone elastomer, hydrogel with a polyethylene jacket, polyvinyl alcohol hydrogel (Aquarelle), polycarbonate urethane elastomer (Newcleus), thermoplastic polyurethane elastomer (such as Tecothane) or other elastomers, polymers, plastics or rubber-like substances, either alone or in combination with these or other materials. In embodiments, inner dampener material exhibits the following characteristics: (i) compliant enough to substantially reduce indentation into the vertebrae and (ii) stiff enough to keep an outer shell from breaking. In embodiments, an interbody device 10 of the present invention will undergo compressive deformation during daily activities and restore itself to near its original form each day during typical daily rest, including at least 98% daily restoration in one embodiment. In one embodiment of the invention an interbody device 10 of the present invention includes a creep modulus that changes by less than 20% in ten years at 37° C. In embodiments of the invention, an interbody device 10 is injection moldable, such as a thermoplastic or thermoset.

In one embodiment, the inner dampener 200 comprises Tecothane brand thermoplastic polyurethane elastomer and the outer shells comprise PEEK-Optima brand carbon fiber reinforced PEEK.

Figure 9:
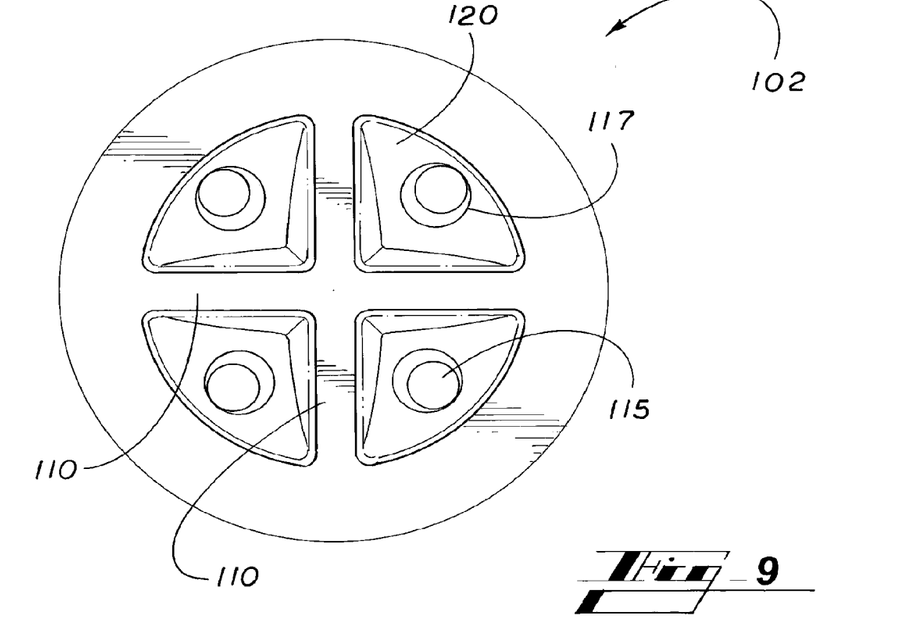
FIG. 9 is a bottom plan view of top outer shell of a spherical interbody device in one embodiment of the present invention.

With reference to FIG. 9, in embodiments of the invention each of outer shells 102 and 104 include a complimentary internal structure to the inner dampener 200. Two crossing ribs 110 segment the internal structure of an outer shell into four concave seating portions 120 that each seat a convex portion 220 of the inner dampener 200. Each seating portion 120 communicates with walled portion 117 of a cylindrical segment of the opening 115. Walled portion 117 is complimentary to inner dampener heads 240 that fill the opening 115 and the head faces 250 provide portions of the contoured outer surface of the device 10 with outer shells 102 and 104.

In one embodiment, ribs 110 are about 1.27 mm thick and the outer shells have a thickness of about 2.03 mm.

Figures 1, 2, 3:
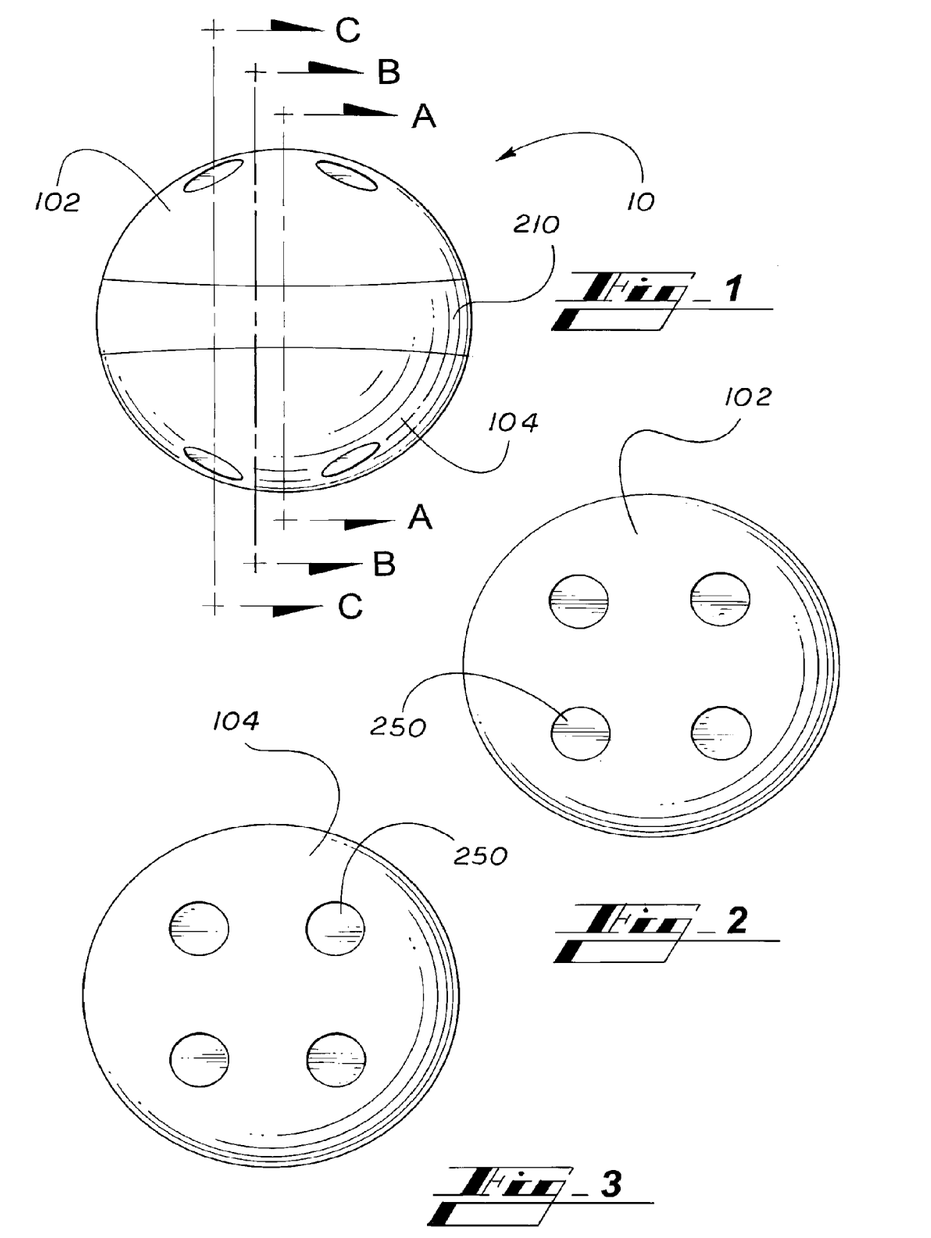
FIG. 1 is a front plan view of a spherical interbody device in one embodiment of the present invention.
FIG. 2 is a top plan view plan view of a spherical interbody device in one embodiment of the present invention.
FIG. 3 is a bottom plan view of a spherical interbody device in one embodiment of the present invention.
Figure 4:
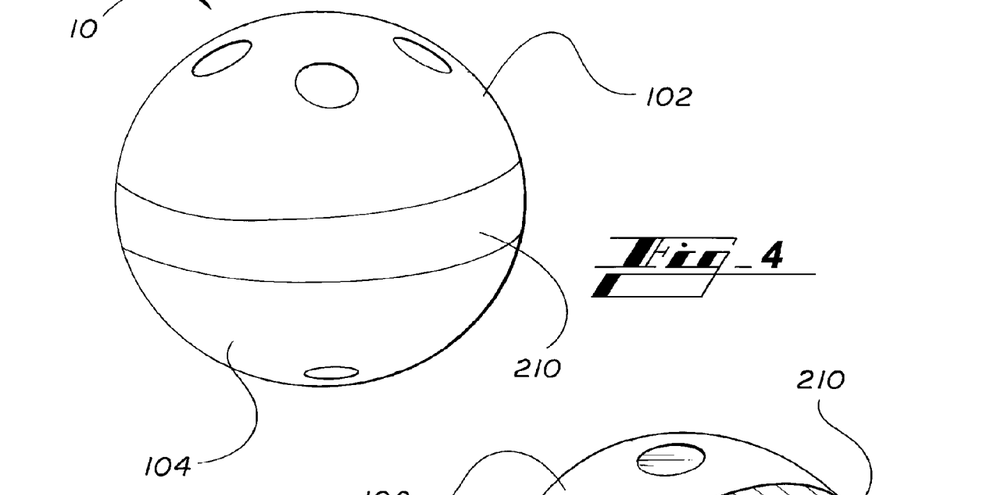
FIG. 4 is a front perspective view of a spherical interbody device in one embodiment of the present invention.
Figures 5, 6:
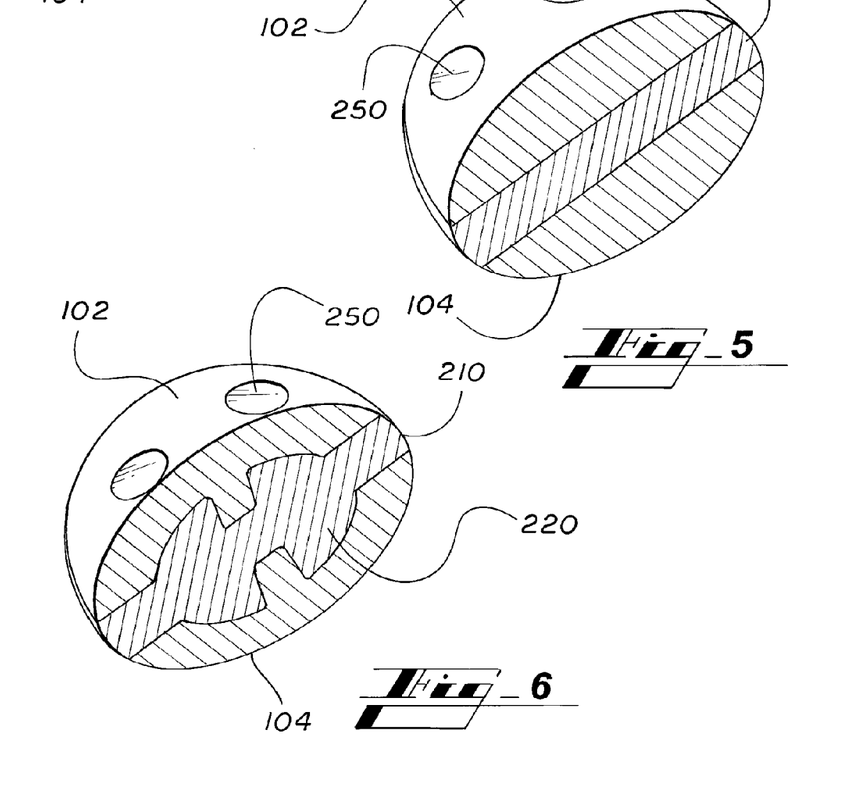
FIG. 5 a cross-sectional perspective view along Section A-A of FIG. 1 in one embodiment of the present invention.
FIG. 6 is a cross-sectional perspective view along Section B-B of FIG. 1 in one embodiment of the present invention.
Figure 7:
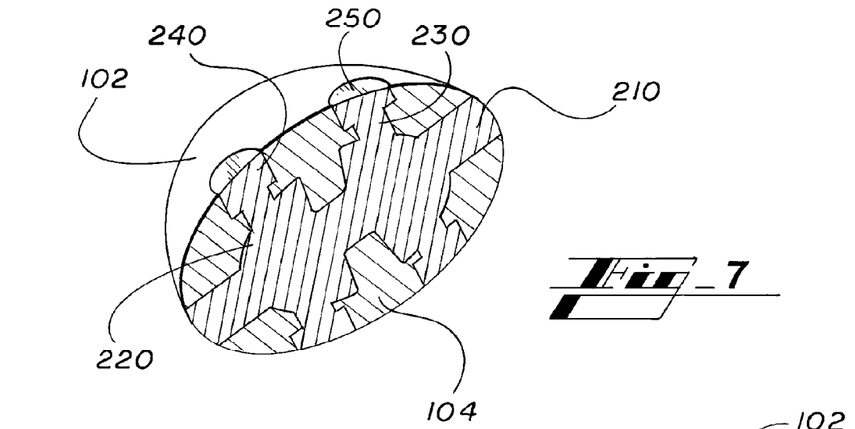
FIG. 7 is a cross-sectional perspective view along Section C-C of FIG. 1 in one embodiment of the present invention.

Referring to FIGS. 5-7, and further reference to FIG. 1, cross-sectional views of assembled interbody device 10 depict the internal molding of inner dampener 200 to shells 102 and 104. Circular rim 210 extends through the middle of interbody device 10 along section A-A (FIG. 5) that depicts the center of the interbody device 10 and between segments 220. FIG. 6 shows segments 220 and rim 210 within shells 102 and 104 along section B-B which cross-sections interbody device 10 outward from its center and before pillars 230 and heads 240. In FIG. 7 section C-C provides a cross-section through two top and two bottom openings 115 moving further outward through the interbody device 10 from sections B-B and A-A. Along section C-C, rim 210, convex portions 230 and heads 240 with faces 250 are shown molded within shells 102 and 104.

In embodiments of the invention, interbody device 10 may have diameters of various sizes, including ranging from about 6 to about 18 mm, although such sizes may be adapted to the particular patient or purpose. In one embodiment, the interbody device has a spherical diameter of about 11 mm.

In various embodiments of the present invention an interbody device 10 may be constructed as one piece or assembled as a unit. In some embodiments of the invention, overmolding processes, including but not limited to injection and/or insert molding, may be used to couple an inner dampener 200 and outer shell materials. In other embodiments, press-fitting, adhesives, mechanical fastening and like coupling means may be used. In alternative embodiments, a mechanical spring or similarly compressible apparatus may be provided in place of or complimentary to an inner dampener 200 or compressible material.

In one embodiment, a molding method is provided for manufacturing an interbody device 10 of the invention. Initially, outer shells 102 and 104 are each injection molded in a mold cavity. Next, shells 102 and 104 are placed into a different mold cavity for creating the inner dampener 200. The dampener 200 is molded with and into the two shells 102 and 104. Finally, the rim 210 is molded onto the three-piece molded assembly in yet another mold cavity. In such embodiment, the interbody device 10 is a four-piece, fully molded-together assembly.

In embodiments, a trimming process may also be utilized where external molding support pegs (not shown) are also used to stabilize the outer shells 102 and 104 during manufacture. For example, a peg may be added to the outside of each shell 102 and 104 on the center surface between openings 115. Such peg holds each shell half in the mold cavity before and during the molding of the compliant inner dampener material. Such pegs may also hold the shell-dampener sub-assembly in the mold for the molding of the rim 210. In one embodiment, a support peg is 3.68 mm long with an elliptical shape and a middle cross-section area equivalent to a cylindrical peg of diameter of 1.04 mm. The supports pegs are trimmed off in the finishing of the interbody device 10, including in embodiments where the outer surface of the interbody device 10 is made smooth.

While the invention has been described with reference to structures and methods in some embodiments of the invention, the invention is not intended to be limited thereto, but extends to modifications and improvements within the scope or equivalence of the claims.

What is claimed is:

1. A method for providing disc nucleus replacement in a spine comprising implanting between two vertebrae an interbody device having an ellipsoidal shape and having a core with at least one convex core portion from which one or more pillars extend outward toward an outer surface of the interbody device, wherein convex outer surfaces of outer shells of the interbody device contact an upper vertebrae and a lower vertebrae, and wherein at least one pillar includes a main pillar portion terminating at a head portion having a larger diameter than the main pillar portion, and wherein the head portion secures an outer shell to the convex core portion.

2. The method of claim 1, wherein said ellipsoidal shape is a sphere.

3. The method of claim 2, wherein the core includes an equatorial planar surface portion providing a thickness at a middle segment of the interbody device.

4. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein the core includes an equatorial planar surface portion providing a thickness at a middle segment of the interbody device.

5. The method of claim 4, wherein at least one pillar includes a main pillar portion terminating at a head portion having a larger diameter than the main pillar portion, and wherein the head portion secures an outer shell to the convex core portion.

6. The method of claim 1, wherein the core includes an equatorial planar surface portion providing a thickness at a middle segment of the interbody device.

7. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein the outer shells include polyetheretherketone molded to the convex core portion including thermoplastic polyurethane elastomer.

8. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein the outer shells each include carbon reinforced polyetheretherketone molded to the convex core portion including thermoplastic polyurethane elastomer.

9. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein the one or more pillars are not coaxial with an axis passing through a center of the interbody device.

10. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein at least one pillar includes a main pillar portion terminating at a head portion having a larger diameter than the main pillar portion, and wherein the head portion secures an outer shell to the convex core portion, and wherein the one or more pillars are not coaxial with an axis passing through a center of the interbody device.

11. The method of claim 1, wherein said ellipsoidal shape is one of an oblate spheroid, a prolate spheroid, and a scalene ellipsoid.

12. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein the interbody device is capable of supporting spinal loads up to 1,000 pounds without damaging operability of the interbody device.

13. A method for providing disc nucleus replacement in a spine comprising implanting between two vertebrae an interbody device having a core with at least one convex core portion from which one or more pillars extend outward toward an outer surface of the interbody device, wherein convex outer surfaces of outer shells of the interbody device contact an upper vertebrae and a lower vertebrae, and wherein at least one pillar includes a main pillar portion terminating at a head portion having a larger diameter than the main pillar portion, and wherein the head portion secures an outer shell to the convex core portion, and wherein the interbody device is capable of supporting spinal loads up to 1,000 pounds without damaging operability of the interbody device.

14. The method of claim 4, wherein the interbody device is capable of supporting spinal loads up to 1,000 pounds without damaging operability of the interbody device.

15. A method for providing disc nucleus replacement in a spine comprising implanting between two vertebrae an interbody device having four upper convex core portions and four lower convex core portions, an equatorial planar surface portion between said upper and lower convex core portions providing a thickness at a middle segment of the interbody device, said convex core portions each having a pillar terminating at a head portion having a greater diameter than a main pillar portion of the pillar, said pillars extending outward toward an outer surface of the interbody device, and wherein an upper curved outer surface of an upper shell of the interbody device contacts an upper vertebrae and a lower curved outer shell surface of a lower shell of the interbody device opposite the upper curved surface contacts a lower vertebrae.

16. The method of claim 15, wherein said interbody device has an ellipsoidal shape.

17. The method of claim 16, wherein said ellipsoidal shape is one of a sphere, an oblate spheroid, a prolate spheroid, and a scalene ellipsoid.

18. The method of claim 4, wherein the convex core portion has more compressibility than the outer shells.

19. The method of claim 4, wherein the convex core portion is coupled to the outer shells by at least one of overmolding, injection molding, insert molding, press-fitting, an adhesive and a mechanical fastener.

20. The method of claim 9, wherein the convex core portion has more compressibility than the outer shells.

\* \* \* \* \*